United States Patent [19]
Yang et al.

[11] Patent Number: 6,087,335
[45] Date of Patent: *Jul. 11, 2000

[54] RNASE-CV (*CORIOLUS VERSICOLOR*)

[76] Inventors: Mable M. P. Yang; George Chen, both of Block, 17B, Fourth Floor, Baguio Villa, The Hong Kong Special Administrative Region of the People's Republic of China

[ * ] Notice: This patent is subject to a terminal disclaimer.

[21] Appl. No.: 09/094,563

[22] Filed: Jun. 15, 1998

Related U.S. Application Data

[60] Division of application No. 08/359,222, Dec. 19, 1994, Pat. No. 5,824,648, which is a continuation-in-part of application No. 07/983,238, Nov. 30, 1992, Pat. No. 5,374,714.

[51] Int. Cl.[7] ............................. A61K 38/00; C07K 17/00
[52] U.S. Cl. .................... 514/14; 514/8; 514/12; 530/322; 530/324; 530/327; 530/350; 530/371; 530/395; 536/123.1
[58] Field of Search .................... 514/14, 8, 12; 530/327, 324, 350, 300, 322, 371, 395, 415, 417, 823; 536/123.1

[56] References Cited

U.S. PATENT DOCUMENTS 5,374,714  12/1994  Yang et al. ............................. 530/350

*Primary Examiner*—Michael P. Woodward
*Assistant Examiner*—Abdel A. Mohamed
*Attorney, Agent, or Firm*—Jerome J. Norris

[57] ABSTRACT

A method of obtaining a novel polypeptide from a crude extraction product of polysaccharide peptide *Coriolus versicolor* comprising: a) boiling a water soluble powder of polysaccharide peptide *Coriolus versicolor*; b) centrifuging a boiled product from step a); c) filtering a centrifuged product from step b); d) purifying a solution from step c) by gel filtration chromatography; e) subjecting the purified material from step d) to HPLC using a reversed-phase at ambient temperature, f) subjecting the purified material from step e) to capillary isoelectrophoresis focusing; g) further purifying this product by HPLC and ionic exchange columns and h) purifying a protein by SDS-PAGE and i) recovering a peptide from 12 Kd to 16 kD. The peptide has the partial amino acid sequence GTAAAKEFERQHM SEQ ID NO:1.

4 Claims, 17 Drawing Sheets

(7 of 17 Drawing Sheet(s) Filed in Color)

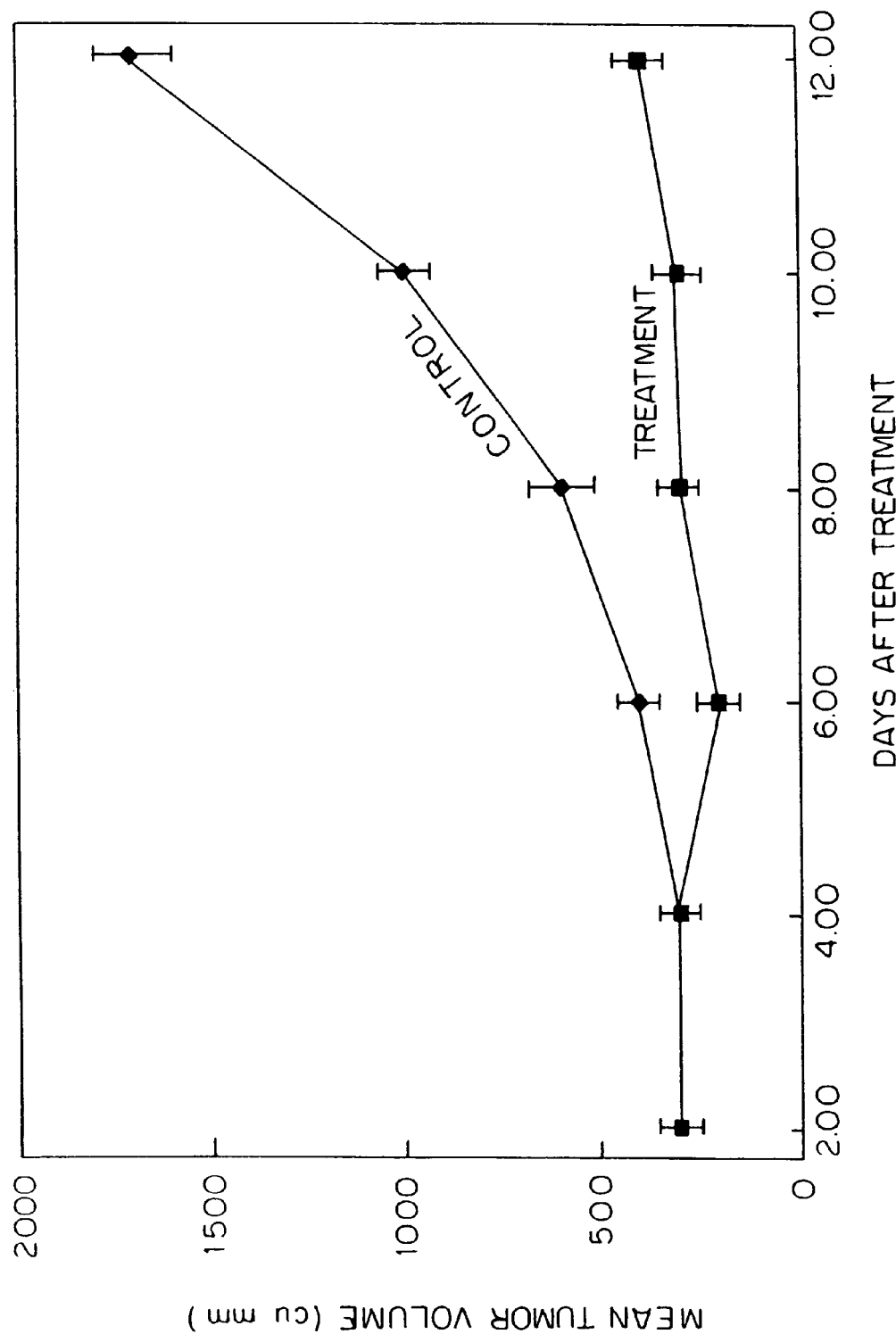

PCV SAMPLE         MARKER

— 97,400

— 66,200

— 45,000

— 31,000

— 21,500

— 14,400

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 13 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (vi) ORIGINAL SOURCE:
      (A) ORGANISM: CORIOLUS VERSICOLOR (xi) SEQUENCE DESCRIPTION: SEQ ID NO:1:

Gly Thr Ala Ala Ala Lys Glu Phe Glu Arg Gln His Met
   1            5                  10

-continued

```
(2) INFORMATION FOR SEQ ID NO:2:

(i) SEQUENCE CHARACTERISTICS:
        (A) LENGTH: 61 amino acids
        (B) TYPE: amino acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Bos taurus ribonuclease
        (F) TISSUE TYPE: Pancreas (xi) SEQUENCE DESCRIPTION: SEQ ID NO:2:

Ile Met Ala Leu Lys Ser Leu Val Leu Leu Ser Leu Leu Val Leu Val
    1               5                  10                  15

Leu Leu Leu Val Arg Val Gln Pro Ser Leu Gly Lys Glu Thr Ala Ala
                    20                  25                  30

Ala Lys Glu Phe Glu Arg Gln His Met Asp Ser Ser Thr Ser Ala Ala
                35                  40                  45

Ser Ser Ser Asn Tyr Cys Asn Gln Met Met Lys Ser Arg
    50                  55                  60
```

RNASE-CV (CORIOLUS VERSICOLOR)

This is a Divisional application of Ser. No. 08/359,222, filed Dec. 19, 1994, now U.S. Pat. No. 5,824,648, which is a Continuation-in-part of application Ser. No. 07/983,238, filed Nov. 30, 1992, now U.S. Pat. No. 5,374,714.

I. FIELD OF THE INVENTION

The invention relates to obtaining purified *Coriolus versicolor*, Cov-1 (PCV) by HPLC (High Performance Liquid Chromatography), after extracting the materials from first and last chromatograph peaks. The purified *coriolus versicolor* polypeptides from these peaks exhibit potent cytotoxic effects on human tumor cell lines but little effect on normal cell lines in vitro and inhibitory effects on the growth of tumor xenografts in Balb/c and nude mice in vivo. Further, the purified *coriolus versicolor* polypeptides possesses immunopotentiating effects, as they increase white blood cells while increasing the amount of T and B lymphocytes, IgG and weights of immune organs. A peptide RNase, extracted from *Coriolus versicolor* Cov-1 isolated from this complex has antitumor activities and immunopotentiating effects. There is no toxic effect when the purified *coriolus versicolor* polypeptides are administered in therapeutic doses, as shown by histo-pathological examination. The purified *coriolus versicolor* polypeptides have utility as anti-cancer drugs and anti immunosuppressive drugs for clinical use.

II. BACKGROUND OF THE INVENTION

Historically, the mushroom has attracted considerable attention as a health-oriented food not only in China and Japan but world-wide. However, during the last decade, the anti-tumor effects of various kinds of mushroom components have been noted as a result of recent research in this field occasioned by the development of new analytical techniques to study the pharmacologically active components from mushrooms [1,2,3,4,5].

[1]. M. Torisu et al., Significant Prolongation Of Disease-Free Period Gained By Oral Polysaccharide K (PSK) Administration After Curative Surgical Operation Of Colorectal Cancer. Cancer, Imm. Imm., 32: 261–168, 1990.

[2]. J. Akiyama et al., Immunochemotherapy Of Transplanted KMT-17 Tumor In WKA Rats By Combination Of Cyclophosphamide And Immunostimulating Protein-Bound Polysaccharide Isolated From Basidiomycetes. Cancer Res. 37:3042, 1977.

[3]. T. Mizuno et al., Antitumor Activity And Some Properties Of Water-Soluble Polysaccharides From "Ilimematsutake", The Fruiting Body Of Agaricus *Blazei Murill.* Agric. Biol. Chem. 4:2889–2896, 1990.

[4]. T. Mizuno et al., Antitumoractive Polysaccharides Isolated From The Fruiting Body Of *Hericium Erinaceum*, As Edible And Medicinal Mushroom Called Yamabushitake Or Houtou. Biosci. Biotech. Biochem., 56: 347–348, 1992.

[5]. "H. Kawagishi et al., Isolation And Characterization Of A Lectin From *Grifola Frondosa* Fruiting Bodies. Bioch. et Biophy. Acta. 1034: 247–252, 1990";

The immunological status of a patient has been recently regarded as an important factor in the control of cancer, especially when there exists only a low tumor burden. This has given rise to the concept of the use of Biological Response Modifiers (BRM) in cancer therapy. The BRM is defined as "drugs that can regulate the relationship between the host and the tumor, leading to a biological response of therapeutic value." Therefore, there is a need extant in the area of treating patients to control cancer (especially where there exist only a low tumor burden) by finding materials capable of exhibiting immunomodulating actions as well as tumor inhibition when used clinically on various types of carcinoma.

In the area of mushrooms, the most potent strain examined was *Coriolus versicolor* in which PSK (polysaccharide Krestin) was extracted from Basidiomycetes and reported from Japan in 1965[6],[7] and PSP (polysaccharide peptide) from Cov-1 (Yun Zhi) reported from China in 1984[8]. Many experimental studies and clinical investigations of PSK[1],[9] and PSP[10] relate to their anti-tumor effect and especially for their potential use in cancer immunotherapy. It was found that the anti-tumor effect of PSP was more potent than that of PSK[11]. In vitro experiments of PSP were reported to inhibit the proliferation of P388 leukemia cells and Ehrlich ascites cells; it also inhibited the proliferations of some human tumor cell lines including SCG-7901, SPC, and SLY (4). In vivo experiments showed that PSP inhibited the growth of murine sarcoma 180 in tumor bearing mice[12]. The immunopotentiating effect of PSP was also noted, and it was seen that PSP increased the thymus weight and the serum C3 and IgG content of tumor bearing mice[13]. Furthermore, PSP promoted lymphocyte proliferation and increased the production of IL-2 and interferon (INF)[14]. A clinical study at the Shanghai Medical University involves 151 cases of various kinds of cancer patients who were treated with PSP, and found noticeable anti-cancer effects without toxicity to the body[10]. Since the PSP used in these studies were in crude extracts, further purifications of PSP are needed, as the mechanism of the anti-tumor effect of PSP was not clear.

[6]. Y. Nakono et al., Influence Of Protein Polysaccharide (PS-K) Isolated From Basidiomycetes On Delayed Hypersensitivity In Sarcoma-180 Bearing Mice, Proc. Japan. Cancer Assoc., 32: 282, 1973.

[7]. S. Tsukagoshi et al., Kretin (PSK) Cancer Treat. Rev., 11-131–155, 1984.

[8]. Q. Yang et al., Isolation Of The Polysaccharide Components Of PSP J. Shanghai Teach. Univ. (Natural Sciences Ed) 4:36, 1986.

[9]. Y. Nio et al., In Vitro Immunomodulating Effect Of Protein Bound Polysaccharide, PSK On Peripheral Blood, Regional Nodes, And Spleen Lymphocytes In Patients With Gastric Cancer. Cancer Imm. Imm. 32: 335–341, 1991.

[10]. T. Liu et al., Clinical Implication Of PSP In Oncology In Recent Advances In Cancer, Published By Cancer Research Group, CUHK, 57–62, 1989.

[11]. X. Li et al., A Study Of Anti-Cancer Effects Of PSP And PSK On Human Tumor Cell Lines In Vitro. Acta Acad. Med., Shanghai, 14:23–24, 1987.

[12]. J. Zhou et al., The Anti-Tumor And Immunomodulating Activity of PSP In Mice, J. Shanghai Teach. Univ. (Natural Sciences Ed.) 3: 72, 1988.

[13]. X. Li et al., "Immunomodulating Actions Of PSP, In Recent Advances In Cancer, published by Cancer Research Group, CUHK, pp. 45–56, 1989.

[14]. X. Li et al., Immune Enhancement Of A Polysaccharides Peptides Isolated From *Coriolus Versicolor*, Acta. Pharm. Sinica, 11: 542–545, 1990.

Antitumor substances from RNase containing sources such as bovine semen, pancreas, human pancreas, various kinds of bacteria have been reported (Newton, 1993). The antitumor effect of such RNase was recently summarized in a review paper (Youle et al 1993). RNase from bovine semen and human pancreas was reported to have immunosuppressive effects. An antitumor effect with a RNase has not been found in mushroom although there were some reports concerning the antitumor and immunomodulating effects of various kinds of polysaccharides peptides from several mushroom (Hotta et al, Cho et al).

The structure and amino acids sequence of any peptide extracted from *Coriolus versicolor* and having the mentioned biological activity has not been described previously. Previously, it was not clear whether the active principle was even a peptide. Since the active principle(s) are not known, it is of interest to find out the exact nature and the structure of such active principle's from *Coriolus versicolor* with antitumor activities.

A major object of the present invention is to provide a method for isolating polypeptides from crude PSP by high performance liquid chromatography (HPLC) and capillary isoelectrophoresis-focusing (CIEF) in order to ascertain the mechanism of the anti-tumor affect of PSP.

Another object of the present invention is to provide polypeptides of *Coriolus versicolor* that provide more potent anti-tumor affects than that of the crude extraction of PSP in which the polysaccharide peptide has a molecular weight of about 100 Kd.

A yet further object of the present invention is to provide purified *Coriolus versicolor* polypeptides having a potent cytotoxic affects on human tumor cell lines but little affects on normal cell lines.

A further object still of the present invention is to provide purified *Coriolus versicolor* polypeptides that possess immunopotentiating affects as they increase white blood cells with increases of T and B lymphocytes, IgG and immune organs's weights, and wherein no toxic side affects are induced when these purified *Coriolus versicolor* polypeptides are administered in therapeutic doses as anti-cancer drugs for clinical use.

Still another object of the present invention is to isolate the active compound from PCV and determine its chemical composition for synthesis.

These and other objects of the invention will become more apparent by reference to the materials and methods hereinafter set forth.

III. BRIEF SUMMARY OF THE INVENTION

In general, the purification method of the invention for obtaining polypeptides from crude cultured polysaccharides peptide (PSP) is obtained by extracting PSP from *Coriolus versicolor* of mycelia COV-1. A water soluble brown powder of PSP is boiled, centrifuged and filtered. Thereafter, the filtered material is purified by gel filtration chromatograph, HPLC and CIEF. Polypeptides are obtained from the purification and subsequently assayed for their anti-tumor activity, both in vivo and in vitro. The aqueous extract of PSP is purified by Sephacryl S-300 column chromatograph at a rate of 3 ml/10 min. in 10 mM sodium phosphate buffer at pH 7.2. Eluents were collected with an automatic fractionating collector, and the contents of each fraction were measured for their optical density—the wavelength corresponding to the light absorption of the peptide linkages.

Analytical HPLC was conducted using a reversed-phase column at ambient temperature, while the column was equilibrated with a buffer. Thereafter, a solvent A of $KH_2PO_4$ and the solvent B of KCL is utilized. The elution system consisted of a linear gradient of methanol applied up to a period of about 40 minutes. Analysis of chromatographic peaks were monitored by adsorbents at 230 nm, 1.0 AUFS for protein analysis and 630 nm 0.02 AUFS for polysaccharide analysis, and fractions were collected by a microfractionator. The eluent of each chromatographic fraction peak on the chromatograph were filter-sterilized and dried under reduced pressure, and the dried samples were prepared for further analysis to identify structural components and to assay their biological activities.

Capillary isoelectrophoresis focusing was then used with a solution ampholyte mixture in order to further identify the structural components of the samples. Gel filtration methods were utilized to measure the molecular weight, where a column with Sephadex G-150 was equilibrated with GBS, PBS, and ABS. The standard proteins utilized as a guide included thyroglobulin (Mr 670,000), bovine gamma globulin (Mr 158,000), chicken ovalbumin (Mr 44,000), equine myoglobin (Mr 17,000) and vitamin B 12 (Mr 1,350).

The purified peptide was precipitated with acetone and lyophilized. The dry peptide was diluted and purified by SDS-PAGE along with certain proteins of known molecular weight as standards. A single band was recovered of about 10–16 Kd and partially amino acid sequenced. The partial sequence is GTAAAKEFERQHM SEQ ID NO:1.

IV. BRIEF DESCRIPTION OF THE DRAWINGS

FIGS. IA and IB show a HPLC analysis of crude PSP, wherein 2 ml of sample was injected into the HPLC system equipped with a reversed-phase column C 18 and was eluted with 10 mM $KH_2PO_4$/methanol solution;

FIG. IA shows a profile of multiple peaks from a first run of the PSP sample on HPLC; and FIG. IB shows a profile of only two peaks resulting from a second run on HPLC. The material from peaks 1 and 6 exhibit very active anti-tumor affects.

FIG. 2 shows the Capillary Isoelectrophoresis Focusing (CIEF) 17 cm×25 μm coated. IEF standard proteins 50 fold dilution, ampholyte mixture detect at 200–360 nm high speed scan mode displayed on 280 nm PI value of standard proteins; cytochrome pI 9.60, lentil lectin pI 7.80, β-lactoglobulin pI 5.10, phycocyanin pI 4.65, Sample of PCV pI 3–4.5.

FIG. 3 shows the molecular weight of PCV (10K) was measured by using gel filtration with Sephadex G-150. This sample was compared with standard proteins. PCV Mr (10K), Thyroglobulin Mr 670 Kd, bovine gamma globulin Mr 150 Kd, chicken ovalbumin Mr 44 Kd, equine myoglobin Mr 17 Kd, vitamin B 12 Mr 1.37 K.

FIG. 4 is a color photograph that shows pretreatment of mice with PCV, in amounts of 2 mg×14 days, ip & iv, before inoculation of human SMMU-7721 (hepatoma cell). The incidence of tumor mass was significantly lower in PCV (10K) pretreated group. In the Control the results were: 3/5; PVC groups (50 μg/ml; 1/4, 100 μg/ml; 0/5, 200 μg/ml; 0/4).

FIG. 5 shows the comparative effects of PCV (10K) on the growth of HL-60 (Leukemia cell), HLF, QZG (human normal fetal lung cells and liver cells). Cells were in the presence of the indicated drug concentration for 48 hrs. + cross indicated the growth inhibitory curve at IC 50. HL-60= 30 μg/ml, HLF=180 μg/ml, QZG=90 μg/ml.

FIG. 7A shows the tumor growth curves of the leukemia tumor of the nude mice with PCV (10K) (40 mg/kg/dose).

Figure 8A:
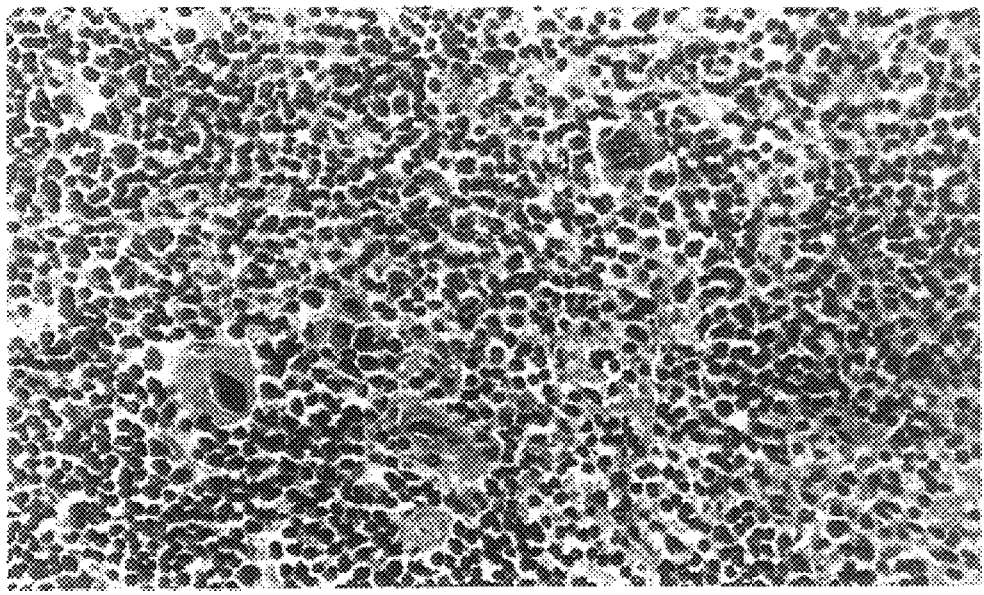
Figure 8B:
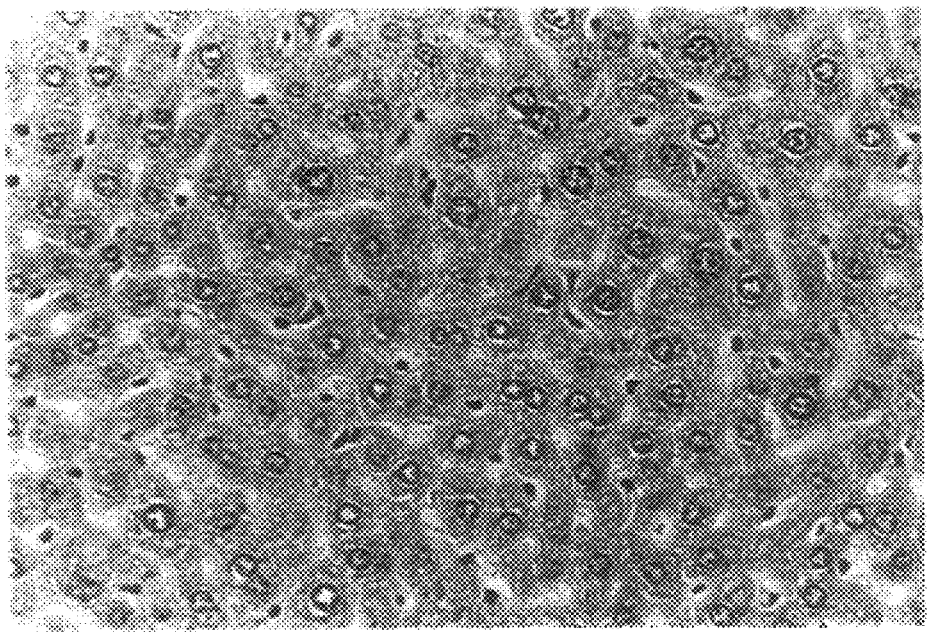

FIG. 8A is a color photograph that shows the pathological analysis (H.E. staining) of the spleen and FIG. 8B is a color photograph that shows the pathological analysis of the liver. Sections are from a mouse treated with PCV (10K) for 4 weeks, and show no pathological lesions. Some polynuclear giant cells appear in (A) at x 40.

Figure 9:
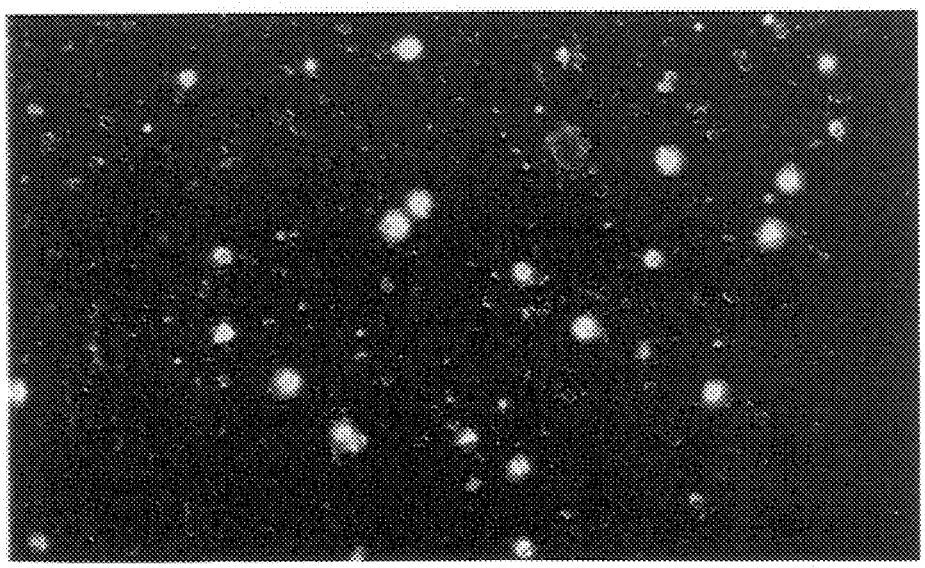

FIG. 9 is a color photograph that shows the fluorescence microscopic analysis of patient lymphocyte with PCV (10K) for 2 months. Cells were isolated from patient blood sample by facoil and than fixed on a slide at a density of $1×10^6$ cells/ml. Anti-neutrophil antibody (CD15) was added to a final dilution of 1:10 for 1 h at 37° C. Then the second antibody (Rabbit anti mouse-FITC) was added for the same duration and concentration. This figure indicated immunofluorescence complex located near the cell plasma and nucleus at x 40.

Figure 10A:
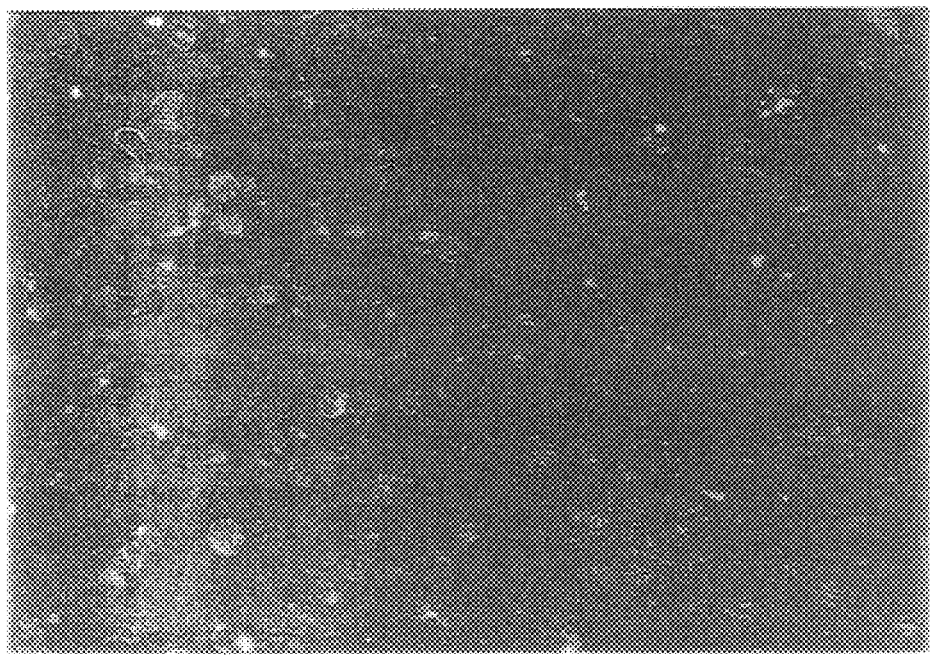
Figure 10B:
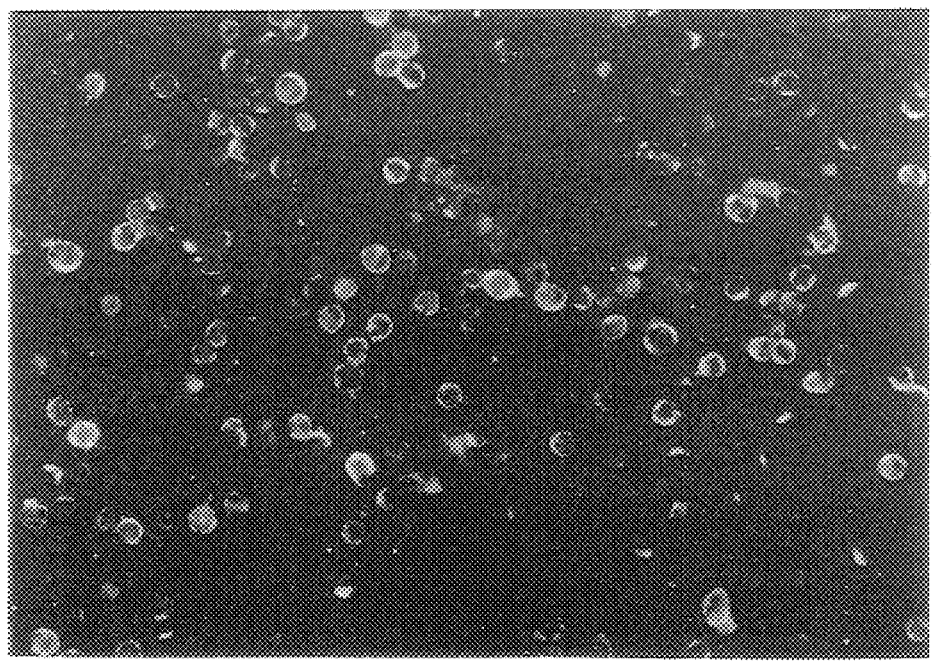

FIGS. 10 A and B are color photographs that show the fluorescence microscopic analysis of mouse lymphocyte treated with PCV (10K) for 4 weeks. Cells were separated from mouse spleen organ by facoil and than attached to a slide at a density of 1×10⁶ cells/ml. Anti B cell antibody (CD37) was added tot a final dilution of 20 times for 1 h at 37° C. Then the second antibody (Rabbit anti mouse-FITC) was added for the same duration and concentration. In particular FIG. 10 (A) is a negative control, and FIG. 10 (B) is positive. It is shown that the immunofluorescence complex is localized mostly in the cell membrane. Some of these are distributed in the cytoplasm at x 40.

Figure 11A:
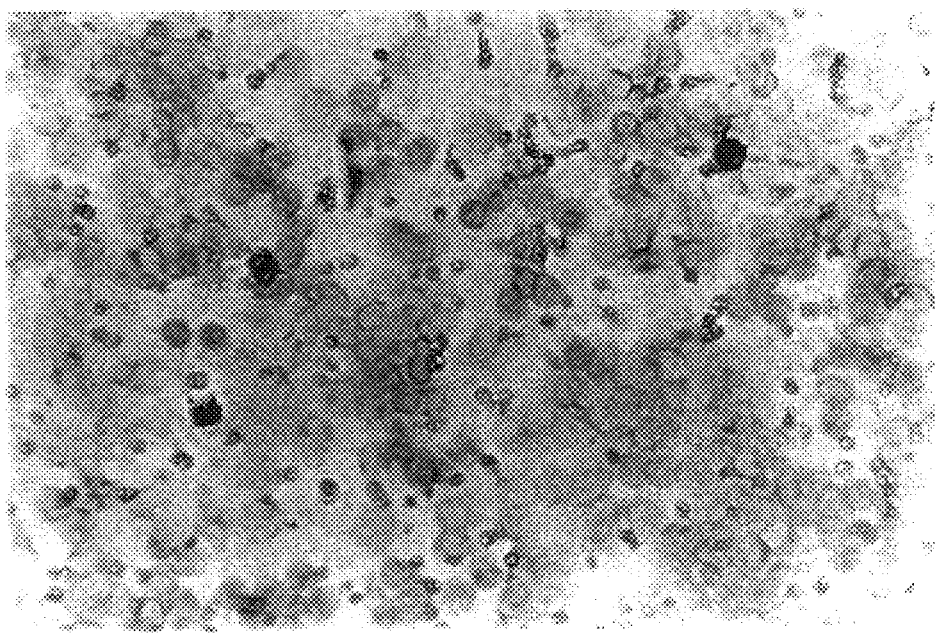
Figure 11B:
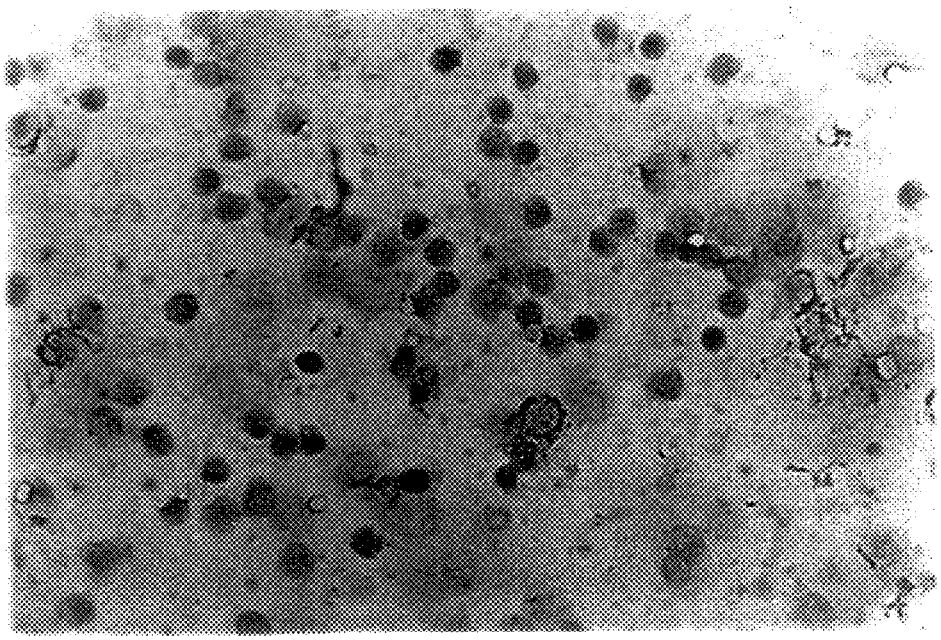

FIGS. 11 A and B are color photographs that show the immunoperoxide staining analysis of patient lymphocyte with PCV (10K) for 2 months. Cells were isolated from patient blood sample by facoil and then fixed on a slide at a density of 1×10⁶ cells/ml. Anti-CD antibody were added to a final concentration of 1:20 overnight at 4° C. This was followed by incubation with a secondary biotinylated antibody (horse anti-mouse or rat) and the avidin-peroxidase complex (Vector), and followed by the addition of DAB, the final coloring agent. FIG. 11A shows CD4 immuno-complex which was located on the whole cell. FIG. 11B shows CD8 immuno-complex which was localized on the cell membrane at x 40.

Figure 12A:
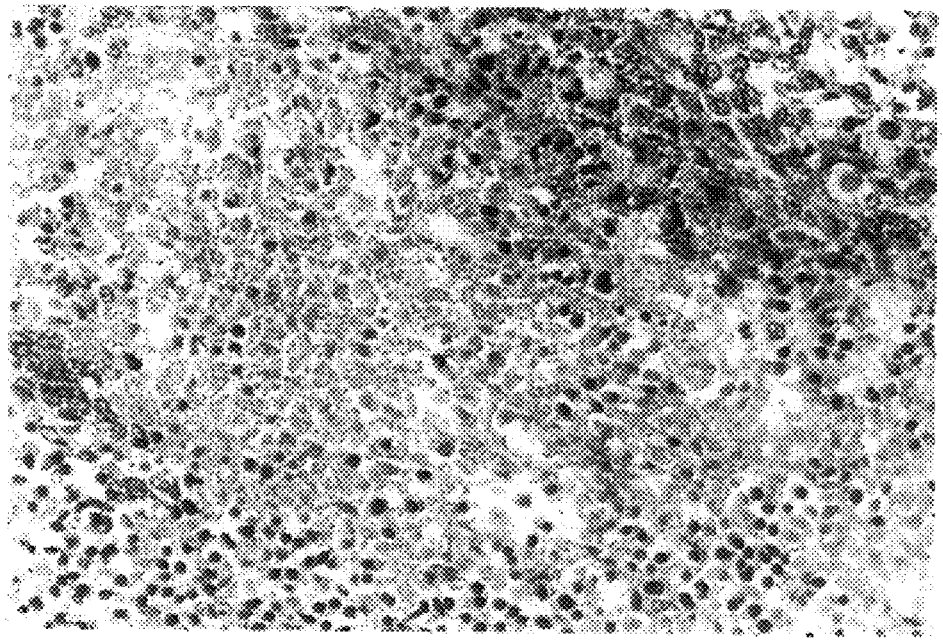
Figure 12B:
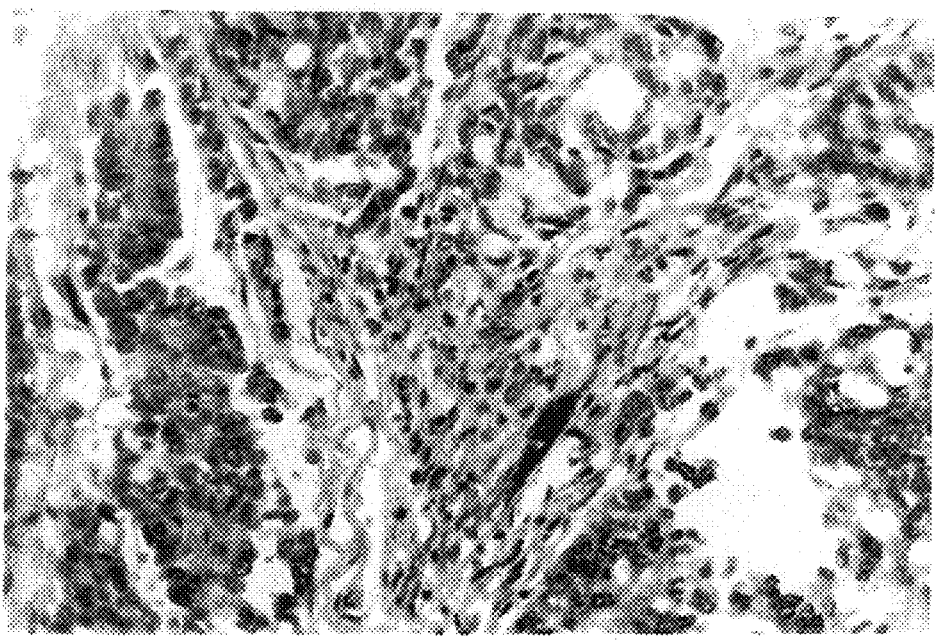

FIGS. 12 A and B are color photographs that show the tumor xenografts, where some tumor cell membranes were found to be disrupted with obscure cytoplasmic structure and increased eosinophilia, representing necrotic alterations (FIG. 12 A). In some cases, postnecrotic fibrous proliferation was encountered at the periphery of tumors (FIG. 12B) at x 40.

Figure 13A:
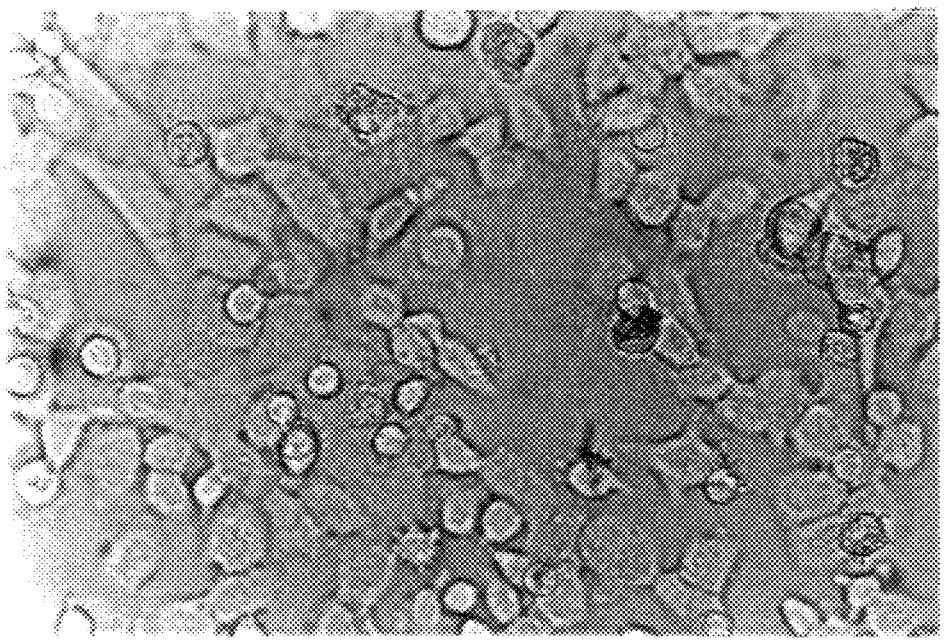
Figure 13B:
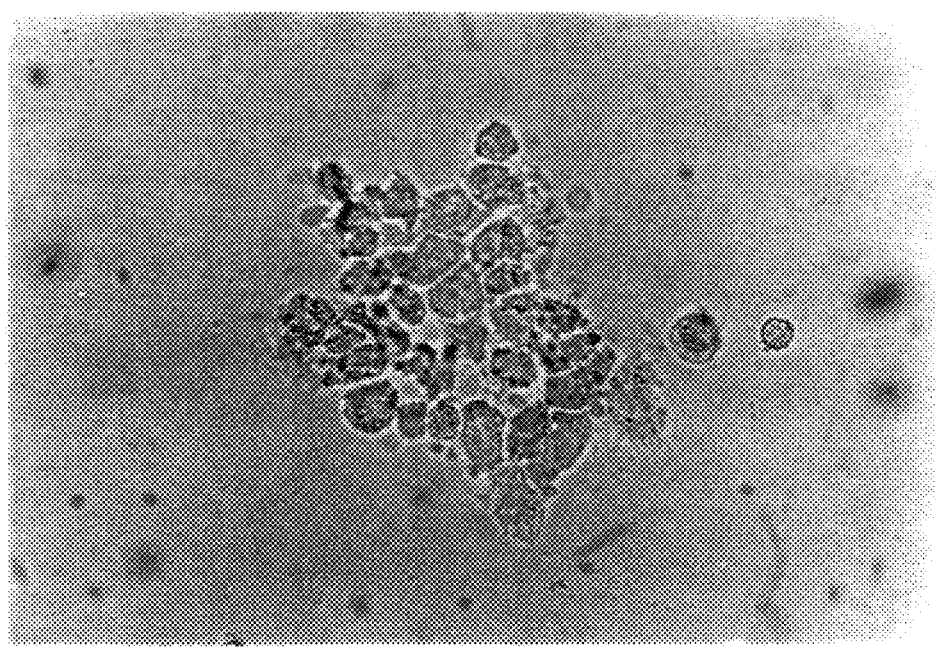

FIGS. 13 A and B are color photographs that show cytotoxic effect of PCV (10K) in culture tumor cells (SCG-7901): FIG. 13A) is a negative control and FIG. 13B) was treated with PCV (10K) for 48 hrs. It is shown that the cells have been subjected to necrosis at x 100.

Figure 14:
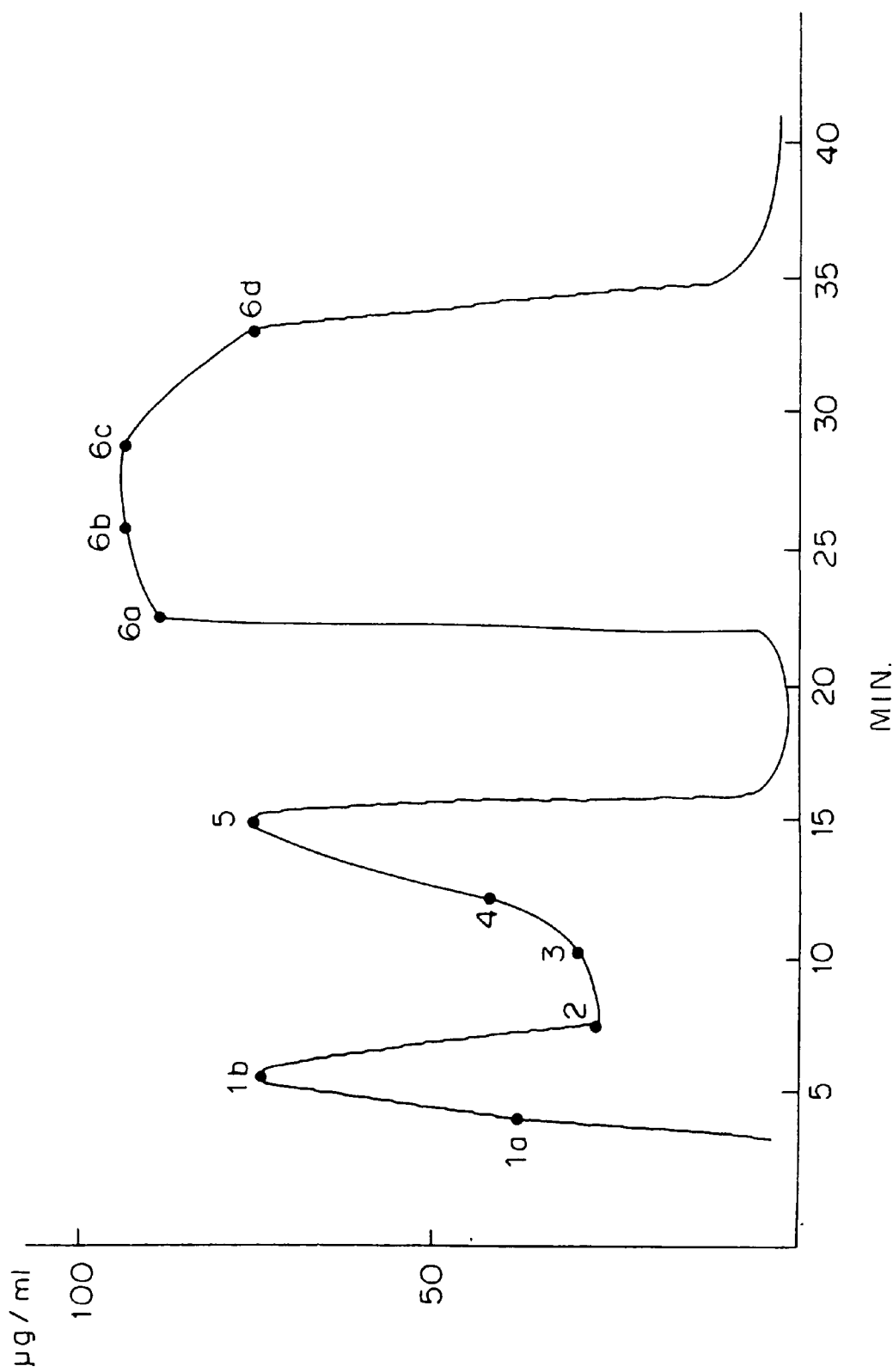

FIG. 14 shows the protein concentration in the eluent of each peak from HPLC with $KH_2PO_4$.

Figure 15:
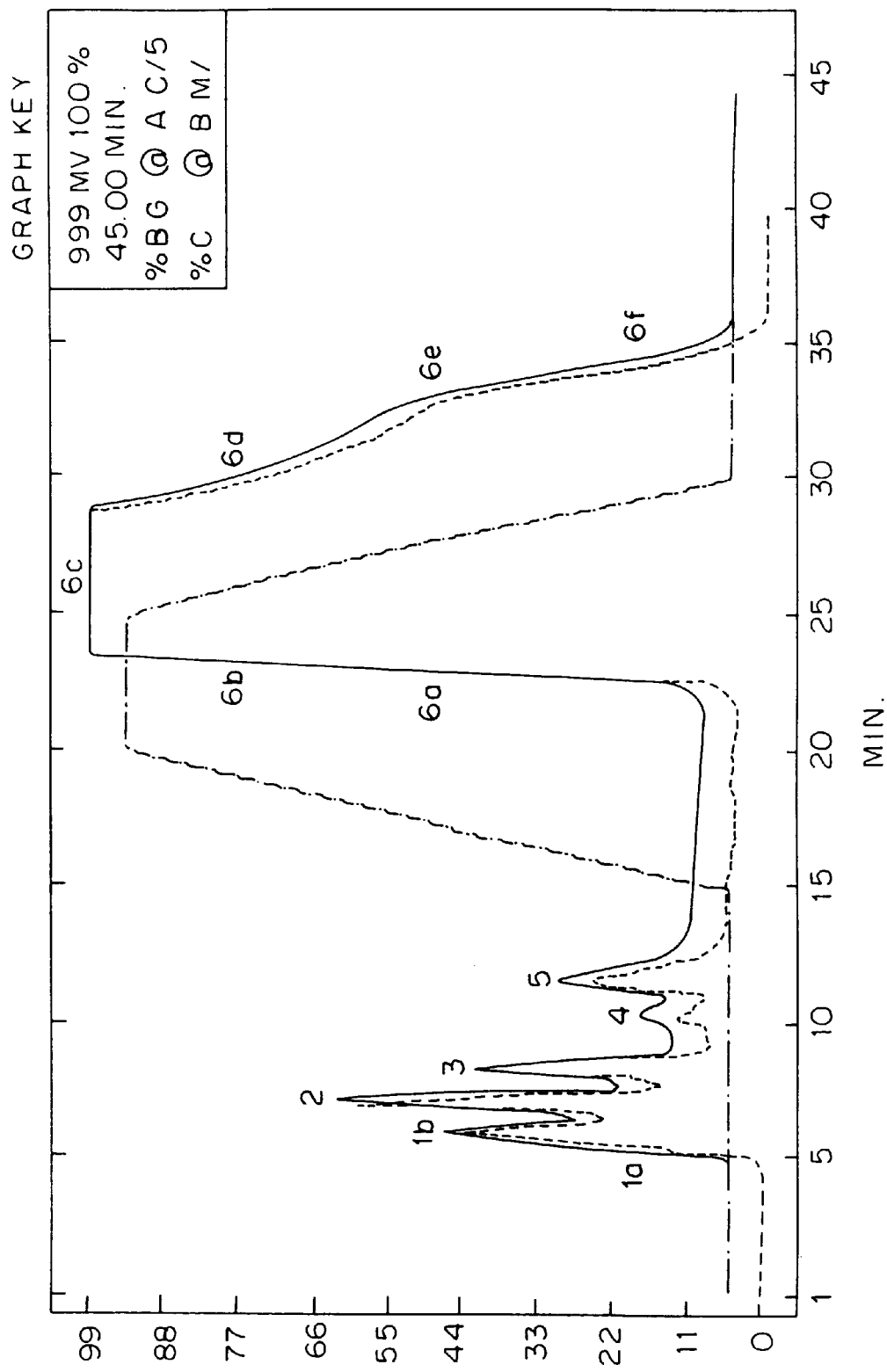

FIG. 15 shows multiple peaks of PSP sample with trifluoroacetic acid (TFA) solvent.

Figure 16:
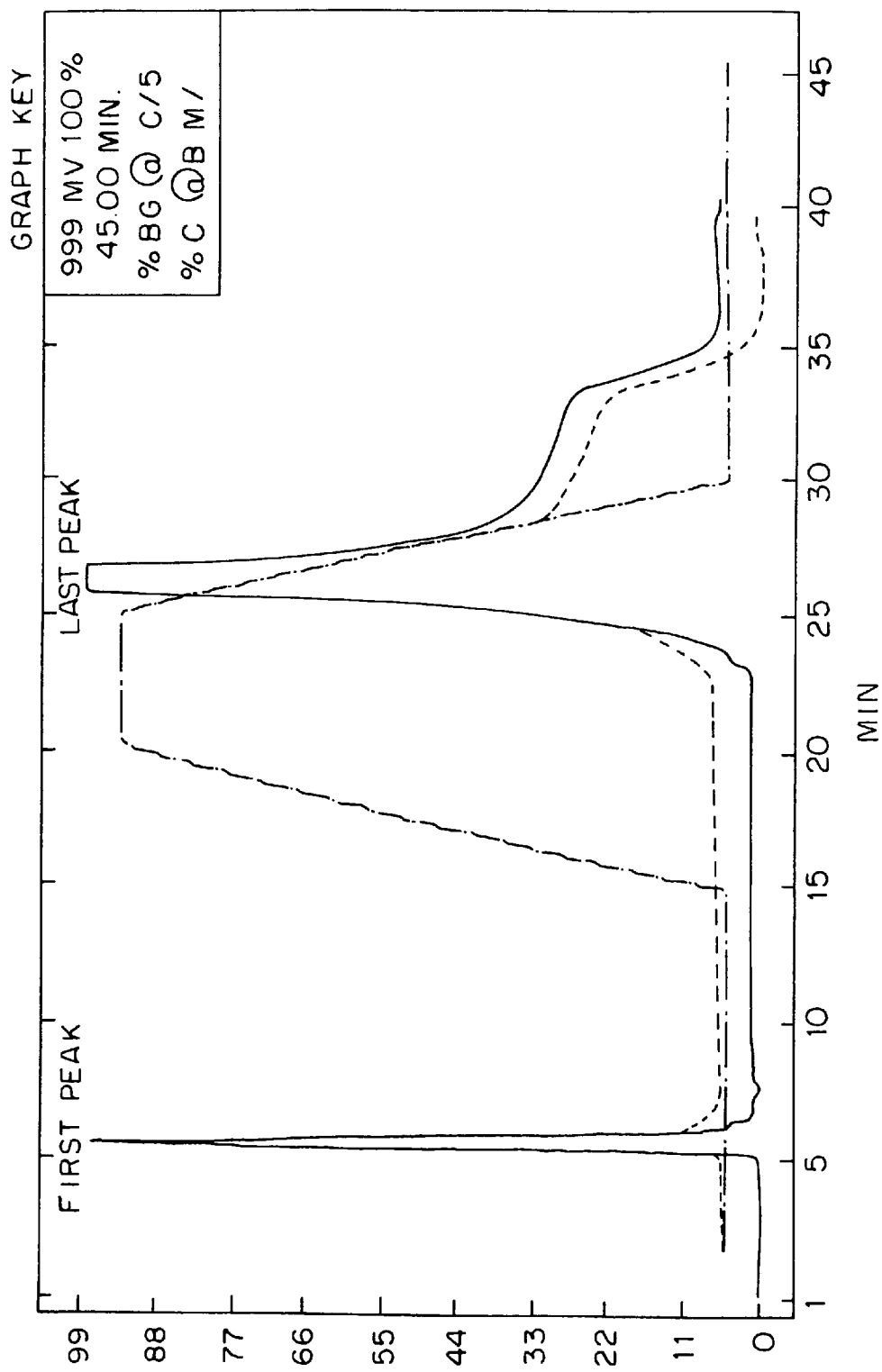

FIG. 16 shows the last peak when the PSP sample was twice subjected to HPLC using the TFA solvent.

Figure 17:
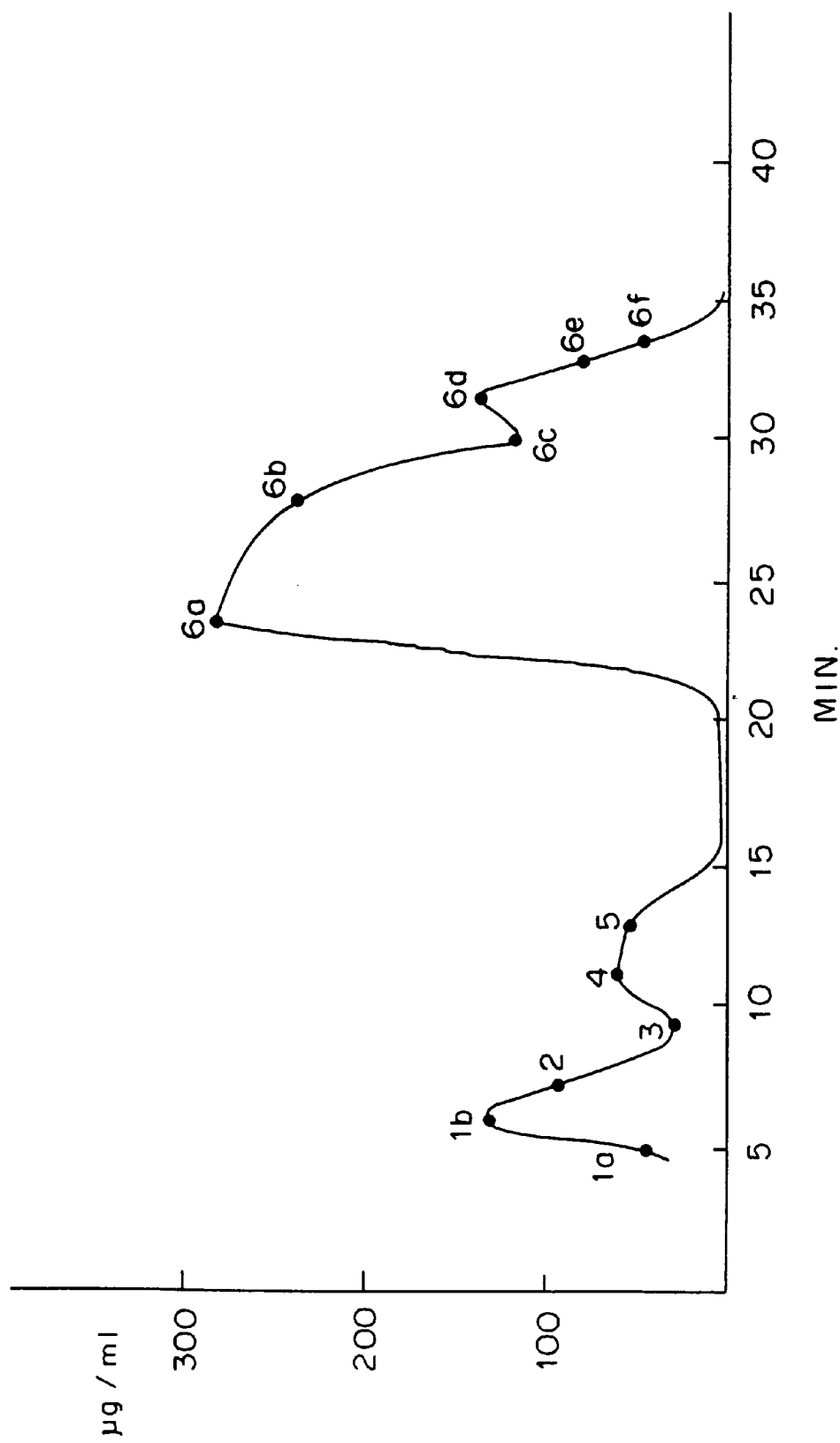

FIG. 17 shows the protein concentration in the eluent of each peak from HPLC with TFA solvent.

Figure 18:
Figure 18:
Figure 18:
Figure 18:
Figure 18:

FIG. 18 shows the peptide band for RNase-CV as compared to other standard molecular weight proteins in a SDS-PAGE (Sodium Dodecyl Sulfate Polyacrylamide Gel Electrophoresis).

V. DETAILED DESCRIPTION OF THE INVENTION

Cultured polysaccharides peptide (PSP) extracted from *Coriolus Versicolor* of mycelia Cov-1 was supplied by the Mushroom Research Laboratory of Shanghai Teachers University. This water soluble brown powder was boiled, centrifuged and filtered. It was purified by gel filtration chromatography, HPLC and CIEF. A small polypeptide was obtained from the above purification and assayed for its anti-tumor activity both in vivo and in vitro experiments after gel filtration column chromatography. The aqueous extract of PSP was first purified by Sephacryl S-300 column chromatograph (Pharmacia Fine Chemicals, Sweden) at a rate of 3 ml/10 min in 10 mM sodium phosphate buffer, pH 7.2. Eluents were collected with an automatic fractionating collector and the contents of each fraction were measured for their optical density at 280 nm. This wave length corresponds the light absorption of peptide linkage.

HPLC

Analytical HPLC (Bio-Rad, model 400) was conducted using a reversed-phase column (carriage of C 18 semi-preparative column) at ambient temperature. The column was equilibrated with a buffer at a flow rate of 4 ml/min. The solvent A composition was 150 mM.

$KH_2PO_4$, pH 6.8 and solvent B was 200 mM KCL. The elution system consisted of a linear gradient of 80% methanol applied from 0 to 40 min. Analysis of chromatographic peaks was monitored by following absorbance at 230 nm, 1.0 AUFS for protein analysis and 620 nm 0.02 AUFS for polysaccharide analysis. Fractions were collected by a Gilson microfractionator. The eluent of each chromatograph fraction peaks on chromatograph was filter-sterilized and dried using a Speed Vac concentrator under reduced pressure. The dried samples were prepared for further analysis to identify their structure components and to assay their biological activities.

Alternatively, Tris buffer at an acidic pH may be used as the aqueous solvent and elution system consists of a linear gradient of 80% methanol applied at a rate of 1 ml/min. between 0–15 minutes. Analysis of chromatographic peaks was monitored by following absorbance at 214 and 280 nm, 1.0 AUFS for protein analysis and collecting fractions of each peak in a microfractionator.

CIEF

Capillary isoelectrophoresis focusing (Bio-Rad, model 3000) was used with a solution of Ampholyte mixture to further identify the structural components of the samples. Gel filtration was used for measuring molecular weight. A column (1.5×96 cm, Bio-Rad) with Sephadex G-150 was equilibrated with GBS, PBS, ABS. Standard proteins were from Sigma Co. (USA) and included thyroglobulin (Mr 670,000), bovine gamma globulin (Mr 158,000), chicken ovalbumin (Mr 44,000), equine myoglobin (Mr 17,000), vitamin B 12 (Mr 1,350). The final products were recovered and named PCV (10K) and PCV (50K) based on the estimated molecular weight of the peaks.

PCV (10K) was further purified using reversed phase HPLC and ionic exchange columns. The eluents fractions detecting a protein peak were separated, further purified with SDS-PAGE and stained with comassie blue and silver staining. Alternatively, the fractions from reverse phase HPLC with or without CIEF were treated with acetone for precipitating the peptide, and then lyophilized. The lyophilized product was diluted and then separated by SDS-PAGE and stained with comassie blue and silver Proteins with known molecular weights were run and compared simultaneously. The molecular weight of PCV (10K) appeared to be from 12 Kd to 16 Kd by SDS-PAGE.

The protein band from SDS-PAGE was isolated and partially amino acid sequenced. The sequence obtained was Gly-Thr-Ala-Ala-Ala-Lys-Phe-Glu-Arg-Gln-His-Met.

Partial Amino acid sequence analysis of purified *Coriolus Versicolor* Cov-1 was performed by using a model 470A gas-phase microsequencer equipped with an on-line phenylthiohydantoin analyzer. Model 120A (Applied Biosystems, Foster City, Calif.). A total of 3.0 mg. of BioBrene Plus (Applied Biosystems) was applied and subjected to three precycles of Edman degradation prior to sample application. PAA derivatives were separated by reversed-phase HPLC on a PTH C18 column Bio-Rad, with a sodium acetate buffer/acetonitrile gradient, on-line, on a model 120A analyzer (Applied Biosystems). The calculated molecular weight of 10–16 Kd was in agreement of previous reports which was determined by gel filtration.

The partial amino acid sequence obtained was compared by a known gene library database to determine whether identical or similar sequences have been determined previously. The partial sequence for RNase-CV is very similar to Bovine pancreatic ribonuclease (EC 3.1.27.5), accession number X072f83. A comparison follows:

```
PCV (RNase-CV)            GTAAAKEFERQHM SEQ ID NO:1
IMALKSLVLLSLLVLVLLLVRVQPSLGKETAAAKEFERQHMDSSTSAASSSNYCNQMMKSR SEQ ID NO:2
    510       520       530       540       550       560
```

The amino acid content of the peptide was determined by Applied Biosystems 477A Protein Sequencer Chromatogram. The results are as follows:

| PEAK ID | R. TIME (min.) | C. TIME (min.) | HEIGHT (uAu) | Pmol |
|---|---|---|---|---|
| ASP | 5.35 | 5.47 | 7035 | 13.55 |
|  | 5.65 |  | 141051 |  |
| ASN | 8.15 | 6.23 | 2088 | 5.49 |
|  | 6.57 |  | 1131 |  |
| SEA | 7.20 | 7.30 | 11961 | 69.11 |
| GLN | 7.68 | 7.73 | 3738 | 14.28 |
| THR | 8.18 | 8.30 | 2067 | 11.59 |
| GLY | 8.53 | 8.62 | 101899 | 490.74 |
| GLU | 9.30 | 9.40 | 3540 | 9.53 |
|  | 9.78 |  | 5949 |  |
| ALA | 12.35 | 12.42 | 13374 | 56.50 |
| HIS | 14.02 | 14.12 | 246 | 5.22 |
| TYR | 16.03 | 16.07 | 4617 | 13.68 |
|  | 16.67 |  | 1332 |  |
|  | 16.97 |  | 2805 |  |
| ARG | 17.87 | 17.92 | 525 | 7.60 |
| PRO | 18.97 | 18.97 | 3837 | 13.90 |
| MET | 18.85 | 19.65 | 1527 | 4.35 |
| VAL | 20.23 | 20.23 | 6372 | 17.64 |
| DPT | 21.77 | 21.75 | 785457 | 3268.47 |
| TRP | 23.00 | 22.92 | 184884 | 386.17 |
|  | 23.33 |  | 4695 |  |
| PHE | 23.77 | 23.73 | 2400 | 7.07 |
| ILE | 24.32 | 24.35 | 2673 | 10.52 |
| LYS | 24.77 | 24.72 | 3729 | 10.26 |
| LEU | 25.70 | 25.15 | 3486 | 12.44 |
|  | 27.87 |  | 2151 |  |

Because of the structural similarity, the protein isolated from PCV was named RNase-CV. However, the chemical and biological properties of RNase-CV are quite different form RNase from other sources. RNase-CV is very acidic and exhibits a pI of about 4. By comparison, most of the RNases from bovine pancreas, bovine semen, human pancreas, bacteria or fungus were basic. RNase-CV has immunopotentiating activity whereas other RNases exhibit immunosuppressive effects. Rnase has a cytotoxic effect on tumor cells but very little toxicity on normal cells compared to other RNases.

While the peptide of the present invention may be produced by extraction from PCV or the mushroom, it may also be chemically synthesized by numerous techniques known per se such as solid phase peptide synthesis. From the pure peptide and partial sequence, the entire amino acid sequence may be determined by conventional further amino acid sequencing or by synthesizing a DNA probe for hybridization to and isolating a genomic DNA or cDNA (from mRNA or a genetic library) from the mushroom which encodes the peptide. This DNA may be sequenced and the amino acid sequence deduced. Such techniques are well known per se. Alternatively, after determining the complete amino acid sequence, a DNA encoding this sequence may be chemically synthesized, and ligated into a suitable expression vector, transformed into a host cell and expressed to yield the peptide RNase-CV. Alternatively, the DNA isolated by hybridization to a DNA probe may be used. Numerous techniques for cloning and expressing a DNA for many genes are well known per se. The same techniques are preferred for producing RNase-CV.

The RNase-CV of the present invention is contemplated for use against a wide variety of animal, mammalian and human cancers, including leukemia, colon cancer, liver, stomach, lung and esophagus cancer. This RNase-CV, may be delivered to the patient intraperitoneally, subcutaneously, intravenously or may be used for targeting therapy. Of the latter, intrahepatic artery administration to liver cancer patient is being carried out. Furthermore, this RNase-CV is going to be conjugated with a monoclonal antibody specific for the cancer cells as a targeting therapy. Any other specific or preferential binding agent, such as a steroid, etc. may be conjugated with RNase-CV as a targeting agent. Conjugation may be by a chemical crosslinking agent or by a fused protein being produced during gene expression.

The RNase-CV of the present invention is also contemplated for use against a wide variety of immunosuppressive conditions such as genetic defects, chemotherapy, radiotherapy, surgery, radiation and chemical exposure and infection, particularly by HIV.

The RNase-CV peptide may be formulated with a number of conventional pharmaceutical carriers for parental administration. Typical carriers include sterile water or saline which may include an oil phase, an emulsifier, another protein such as serum albumin etc. The RNase-CV peptide may be microencapsulated, adsorbed or otherwise bound for slow, delayed or controlled release. An agent for reducing the immunogenicity of the peptide may also be added.

The peptide may constitute from 0.001% to 99% of the pharmaceutical formulation. A dosage of the pharmaceutical used to treat a patient may be from 1 $\mu$l to 1 l. The pharmaceutical formulation and dosage may be further modified according to the patient's need and will vary depending on the patient, his condition or the disease being treated. Such formulation and dosage are readily determined by one skilled in the art.

In Vitro Experiments

A. Cultivation of cell lines.

Cell lines obtained from standard stock culture were seeded in triplicate on microtiter cell plate dishes, test tubes or flasks and cultured for 18 hr (5% $CO_2$; 95% air at 37° C.) to allow cell growth and attachment before starting the assay. The culture medium was RPMI 1640 medium supplemented with 10% fetal calf serum, 2 ml glutamine, 50 IU/ml penicillin, 0.1 mg/ml streptomycin and 10 mM HEPES buffer (pH 7.4). Cells were subcultured once a week at a split ratio of 1:10 using trypsin/EDTA solution and were regularly checked for mycoplasma contamination.

B. Cytotoxic effect and inhibition assay on tumor cells

The growth of tumor cells were detected under microscope after 18 hr incubation at 37° C., in a $CO_2$ incubator. Cells (2–4×10$^9$) were transferred into 55 ml flat bottom test tubes and samples of purified PSP or PCV in different concentrations were added. After incubation for 24, 48, and 72 hours the number of viable cells were determined. The influence of PSP on the inhibition of tumor cells was evaluated by measuring. $^3$H-thymidine incorporation into nuclei DNA of tumor cells. TdR was converted via the salvage pathway to thymidine triphosphate (dTTP) which is incorporated into DNA. Tumor cells which were harvested 7 days after incubation were collected by centrifugation and washed with fresh Hanks solution. Cells were then seeded in 96 well plates (Falcon), 3–5 replicate wells were used for each experimental condition. PCV (10K) samples of different concentrations were added into the wells and incubated for at least 24 hr. $^3$H-thymidine (specific activity, 1 $\mu$Ci/mM) was added to the wells and incubated with the cells for 18 hr before measurement. Cells were detached from the bottom of the test tube by shaking with a shaker. Cells were then lysed by freezing and collected by filtration on membrane filters (pore size, 0.22 $\mu$m); cells were harvested on filter membranes using an automatic cell harvester. The filters were dried and radioactivity on each filter was measured. The cellular $^3$H thymidine uptake was determined by measuring the radioactivity incorporated into DNA using a liquid scintillation fluid and a beta-scintillation counter. The inhibitory rate of incorporation of labelled precursors were calculated according to formula as follows.

$$\text{Inhibition \%} = \left(1 - \frac{\text{cpm of treated group}}{\text{cpm control group}}\right) \times 100$$

The results were also expressed as $IC_{50}$ values. The median concentration of drug required to inhibit the growth of tumor cells by 50% was determined by plotting the logarithm of the drug concentration vs. the growth rate (percentage of control) of the treated cells.

In Vivo Experiments

A. Mice

Six-week old nude mice and Balb/C mice of both sexes, weighing 18–22 g were used as the tumor. Tumor bearing mice. Tumor cells were obtained from standard stock culture in RPMI-1640 medium, supplemented with 10% fetal calf serum, and used as inocula for in vivo growth. Tumor cells (1×10$^6$) were inoculated into nude mice or Balb/c mice.

B. Experiments

The anti-tumor activities of drugs PCV or PSP were assessed in different groups of mice and are described hereafter. Anti-tumor activity was assessed in terms of tumor weight and volume. Tumor diameter was serially measured with calipers to estimate tumor size. The calculation used the following formula: Square root of long diameter×short diameter (mm). Each experimental and control group consisted of 6–10 mice. The difference in tumor growth (tumor size or tumor weight) between the control and experimental groups was tested statistically by using Student's t-test.

For evaluation of the preventive effect of the drug on tumor growth, tumor cells were inoculated at one to two weeks after drug administration. While in the study of the therapeutic effect the drug was given 10 to 15 days after inoculation of tumor cells when tumor lump sizes reached about 5×5 mm$^2$, which could be felt by finger palpation. The drugs effects were evaluated according to the percentage of tumor growth and the inhibition on the tumor growth rate. Serum IgG was measured by using a modified radial immunodiffusion method[15].

[15]. Q. Yang et al., The p- io-Chemical Characteristics Of The Polysaccharide-Peptide (PSP) Of *Coriolus versicolor* (Yun-Zhi) In Recent Advances in Cancer, published by Cancer Research Group, CUHK, pp 7–18, 1989.

Purification of PSP and isolation of PCV

Purification of PSP was done by using gel filtration chromatography, HPLC and CIEF. A small polypeptide was isolated from crude extraction of PSP (*Coriolus versicolor*) and thus, named PCV (polypeptide of *Coriolus versicolor*).

Figure 1A:
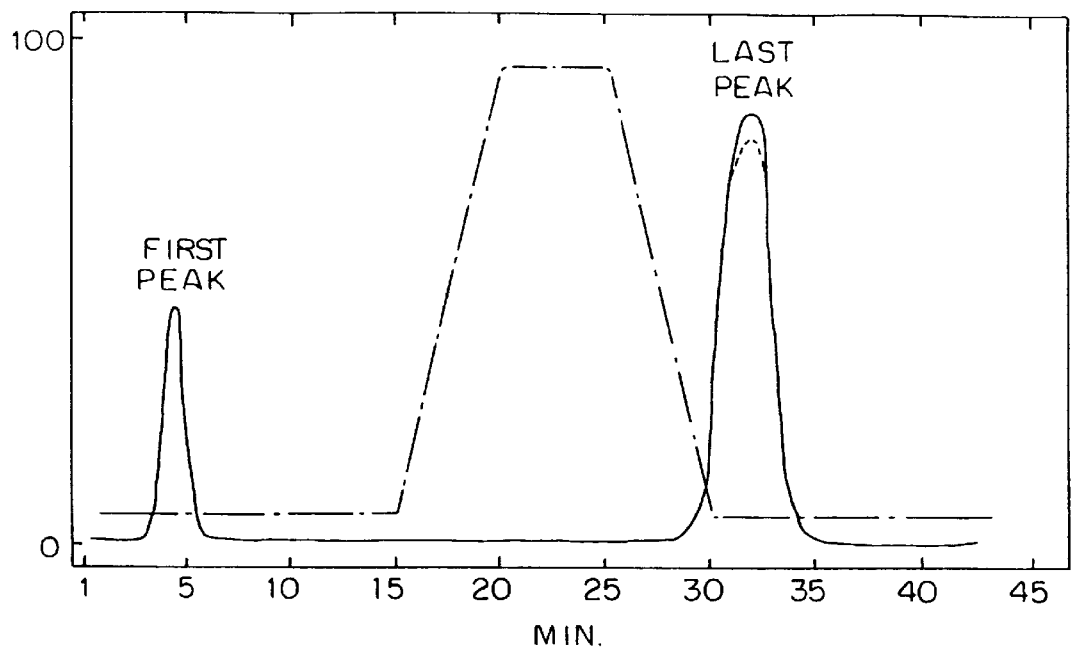
Figure 1B:
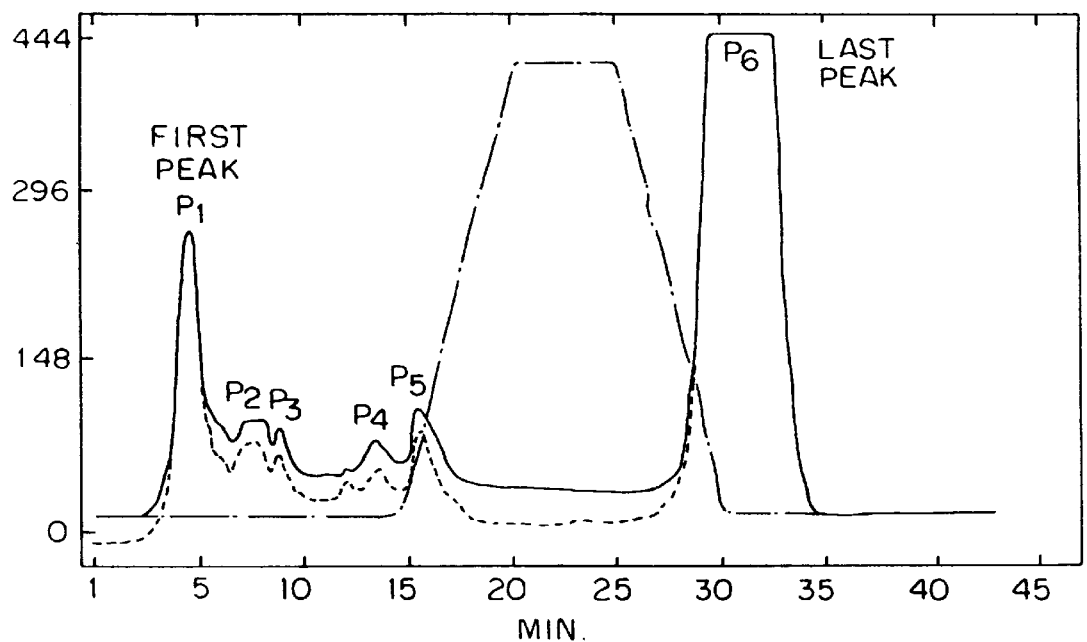
Figure 2:
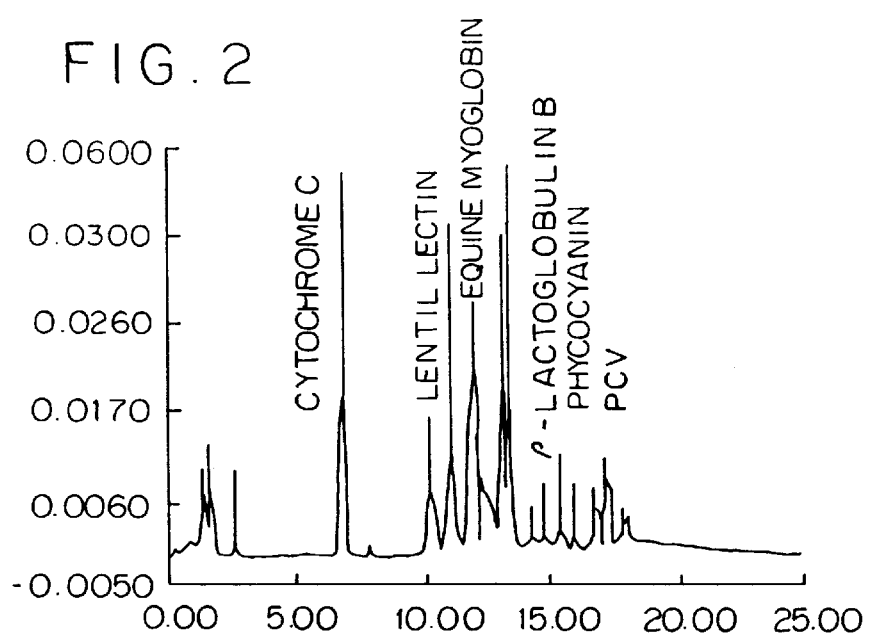
Figure 3:
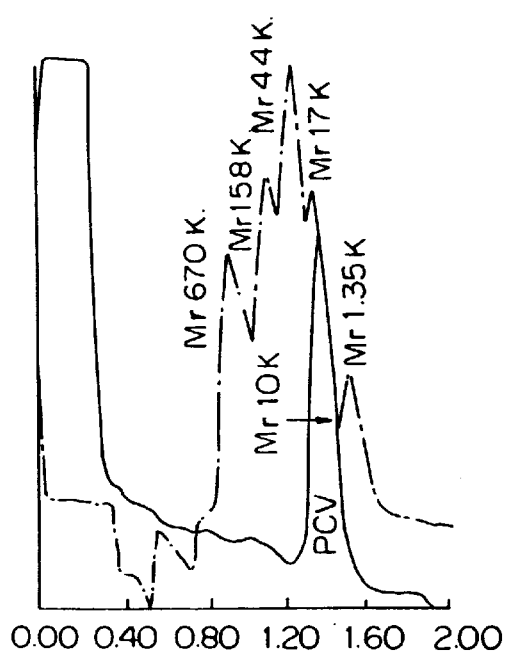
Figures 4, 6B:
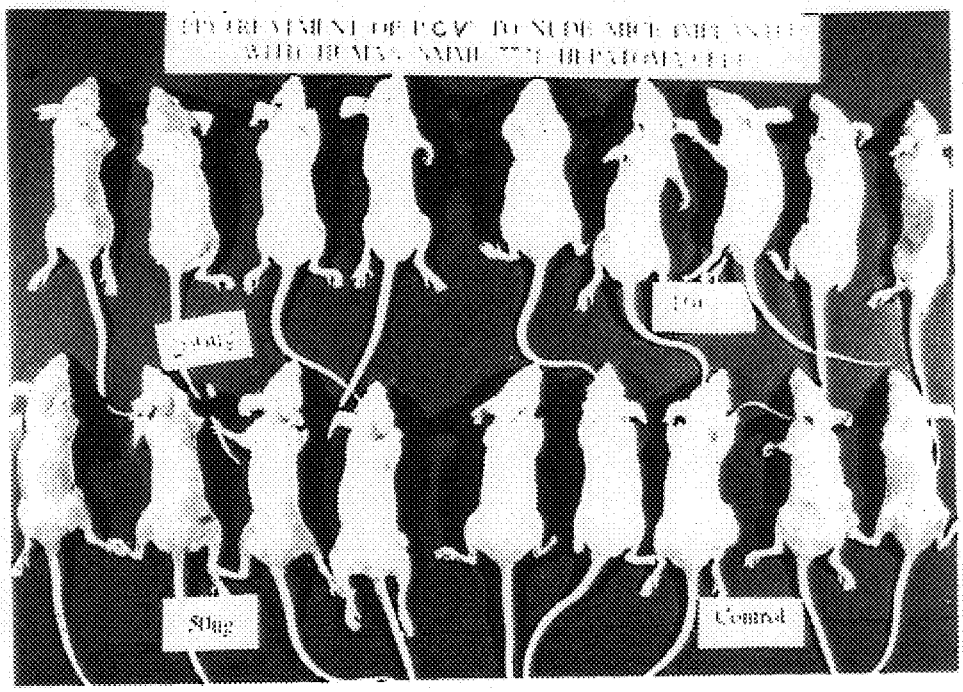
FIG. 6B is a color photograph that shows the treatment effect of PCV (10K) on tumor mass of myeloma cell (Sp2/o) in Balb/c mice. The control tumor mass is 6 times more than PCV (10K) treatment group.
Figure 5:
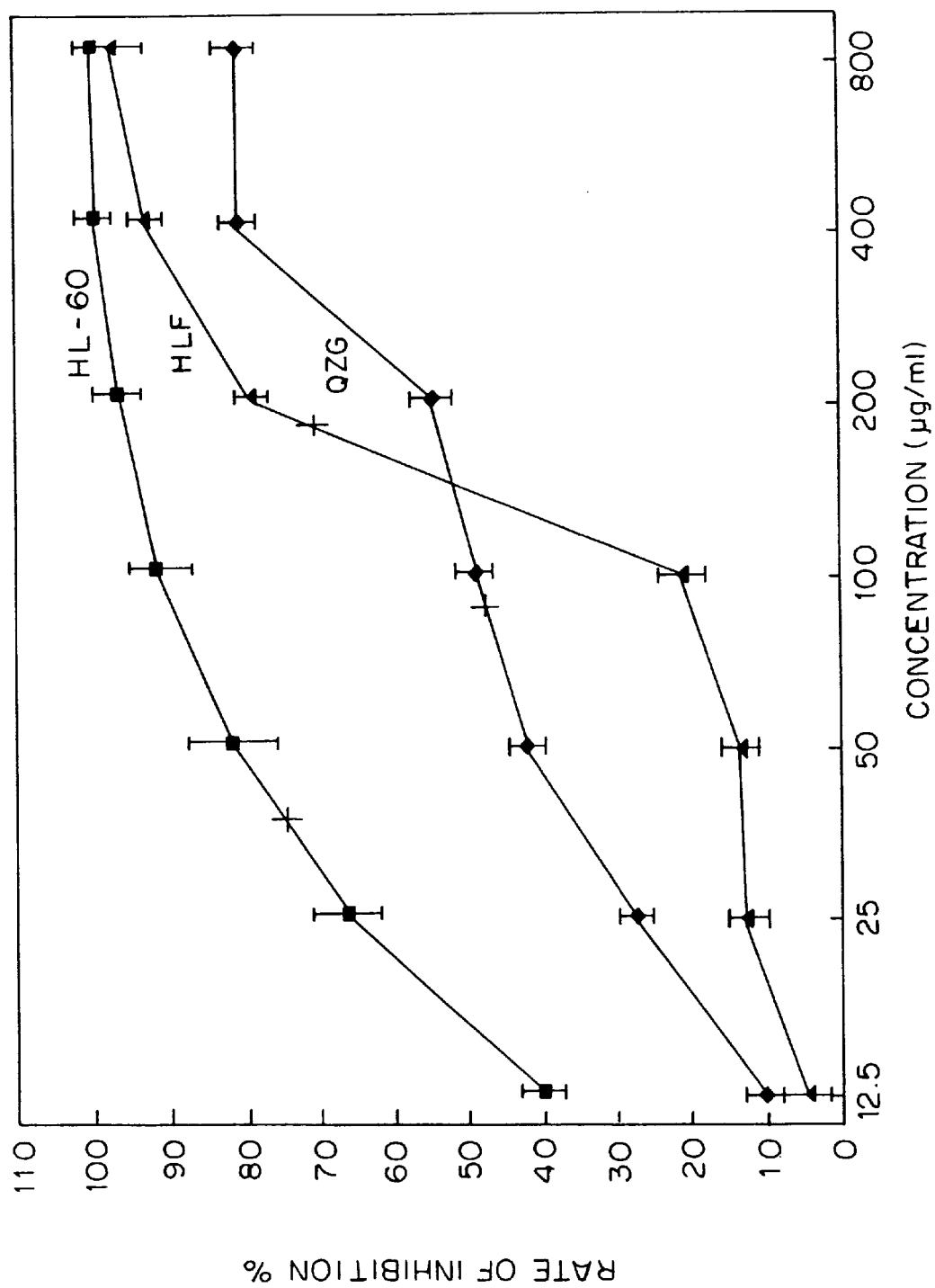
Figure 6A:
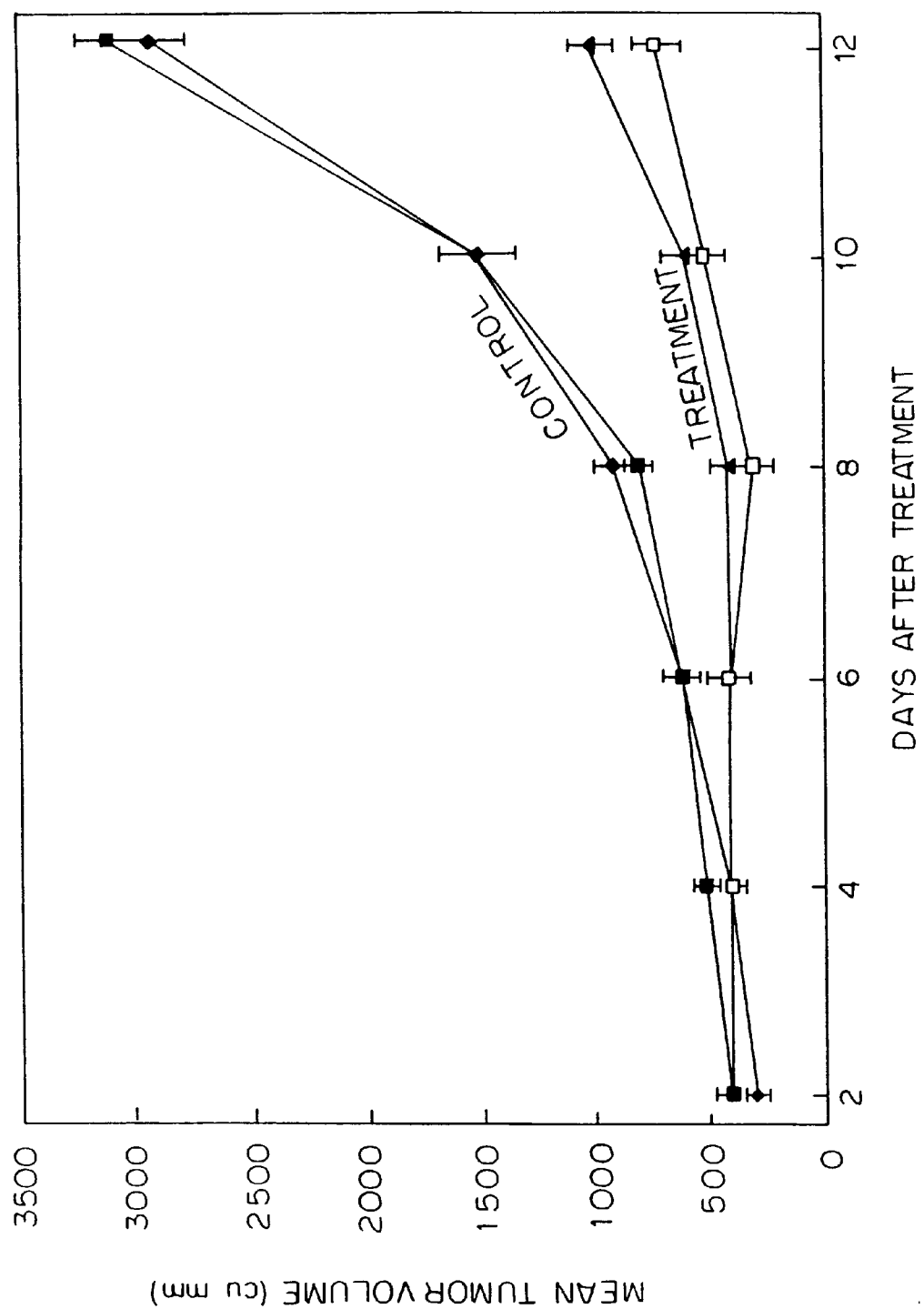
FIG. 6A shows the tumor growth curves of the Sp2/o myeloma tumor of the Balb/c mice with PCV (10K) (40 mg/kg/dose).
Figure 7B:
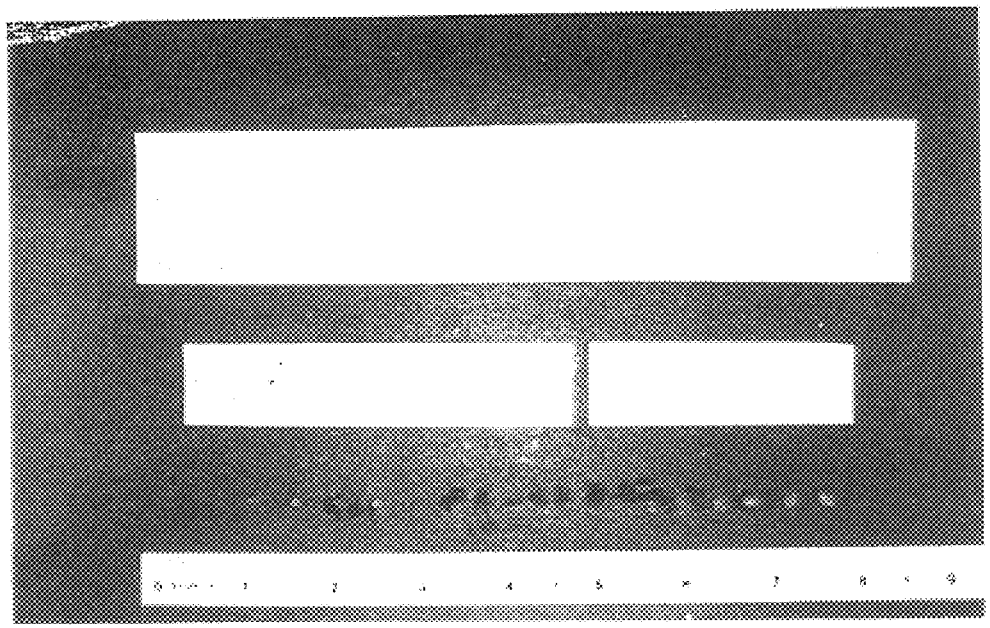
FIG. 7B shows the treatment effect of PCV (10K) on tumor mass of leukemia cell (HL-60) in nude mice. The control tumor mass is 6 times more than treatment group.

Reference is now made to FIG. 1 which shows six peaks; however, the inhibitory effect of different fractions of PSP will show that peak numbers 1 and 6, which contain PCV polypeptides of 10 K and 50 K respectively are the most active in providing potent anti-tumor effects on many human tumor cell lines but little affect on normal cell lines.

TABLE 1

Inhibitory effect of different fractions of PCV (10K) from HPLC on the growth of leukemia cells (HL-60)

| Peak No. | 1 | 2 | 3 | 4 | 5 | 6 |
|---|---|---|---|---|---|---|
| Fraction No. | 7–11 | 12–15 | 19–21 | 24–26 | 27–29 | 46–70 |
| Growth inhibition % | 90 | 71 | 53 | 53 | 49 | 64 |

PCV (10K) was isolated from peak one (1), and PCV (50K) was isolated from peak six (6). Incubation time 48 h. Control RPMI-1640.

In FIG. 1, there are at least two significant peaks from the standpoint of the invention, and they are peaks 1 and 6, which are enlarged or emphasized as follows in order to demonstrate there inhibitory rate on the growth of leukemia cells (HL-60):

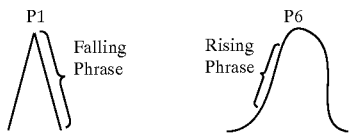

|  | Peak 1 (Falling Phase) | Peak 6 (Last) (Rising Phase) |
|---|---|---|
| Inhibitory rate on HL-60 | 50% | 60% |
| Dosage | 1 $\mu$g/ml | 1 $\mu$g/ml |

TABLE 2

Effect of PCV (10 K) on tumor metastases of nude mice implanted with human rectal carcinonia into kidney capsule

|  | Tumor weight | |
|---|---|---|
|  | Tumor inside Kidney capsule | Tumor metastases outside kidney |
| Saline N = 7 | 0.015 ±0.004 | 0.097 ±0.044 |
| PCV (10K) | 0.016 ±0.007 p > 0.05 | 0.025 ±0.016 p < 0.001 |

<Tumor transplanted at two weeks after treatment>

| 0.001 |  | 0 | 2 weeks | 4 weeks |
|---|---|---|---|---|
| Neutrophil (%) | Saline (N = 4) | 1.3 +0.55 | 4.0% +0.94 | 9.0% +4.3 |
|  | PSP (N = 5) | 1.8% +0.65 | 31.4%** +0.84 | 9.6% +0.57 |
| WBC (cu mm3) | Saline (N = 4) | 6650 +536.5 | 7400 +327.4 | 7900 +1689.3 |

-continued

<Tumor transplanted at two weeks after treatment>

| 0.001 | | 0 | 2 weeks | 4 weeks |
|---|---|---|---|---|
| | PSP | 6840 | 12910** | 8160 |
| | (N = 5) | +336.5 | +1413.5 | +540.5 |

*Weeks after treatment. PSP given 2 mg/day (i.p.) × 10 days
Tumor transplanted at two weeks after treatment.

The T4, T8 numbers increased by 20% over the pretreatment.

TABLE 3

EFFECT OF PSP ON WHITE BLOOD CELLS (WBC).
SERUM IgG LEVELS IN MICE

| | CONTROL (SALINE) | PSP |
|---|---|---|
| WBC | +3100 | +7530* |
| IgG ($\mu$g/L) | +3288 | +6225* |

N = 40
*P < 0.001
psp-S(1P): 2 mg/DAY × 10 DAYS

TABLE 4

Comparison of the inhibitory effect on
HL-60 cell between PCV (10 K), PSP & PSK

| | Inhibitory rates % (X ± SD) | | |
|---|---|---|---|
| | 100 | 400–500 | 800–1000 |
| PCV (10 K) | 91.2 ± 2.26 | 99.3 ± 0.10 | 99.5 ± 0.10 |
| PSP | 11.7 ± 11.6 | 78.8 ± 18.0 | 87.4 ± 16.0 |
| PSK | 57.7 ± 28.9 | 33.0 ± 31.0 | 13.5 ± 18.0 |

*Dosage: $\mu$g/ml
$^3$H TdR incorporation time: 24 hrs.
Time of drug treatment: 48 hrs.

TABLE 5

Inhibitory effect of PSP-K on [$^1$H] TdR incorporation
(into nucleic acid) in tumor*

| | Inhibition % X ± SD | | | | |
|---|---|---|---|---|---|
| PSP-K ($\mu$g/ml) | HL-60 | LS-174T | SMMU-7721 | SCG-7901 | CNE-12 |
| 50 | 81.5 ± 4.79 | −9.3 ± 12.4 | 31 ± 3.6 | −17.9 ± 49.3 | −20.3 ± 16.7 |
| 100 | 91.2 ± 2.26 | 18.3 ± 4.9 | 44.0 ± 4.4 | −13.6 ± 13.2 | −65.0 ± 31.0 |
| 200 | 96.4 ± 1.58 | 68.5 ± 4.8 | 69.7 ± 7.2 | −22.4 ± 46.9 | −57.0 ± 23.0 |
| 400 | 99.3 ± 0.10 | 89.3 ± 1.5 | 77.5 ± 0.7 | 64.2 ± 19.0 | −34.0 ± 24.0 |
| 800 | 99.5 ± 0.10 | 89.3 ± 1.1 | 73.0 ± 2.6 | 86.0 ± 4.10 | |

*[$^1$H] TdR incorporation time: 24 hrs.
PSP-K treatment time: 48 hrs.

TABLE 6

EFFECT OF PSP ON ORGAN WEIGHT IN MICE

| ORGAN (Mg) | CONTROL | PSP |
|---|---|---|
| LIVER | 1377.8 ± 220.63 | 1658.9 ± 15.94* |
| SPLEEN | 163.8 ± 46.52 | 317.2 ± 51.32* |
| THYMUS | 45.7 ± 11.16 | 55.1 ± 21.65 |
| KIDNEY** | 145.0 ± 9.00 | 150.0 ± 17.00 |

*P < 0.05; **KIDNEY (L + R); PSP 5 mg × 14 days, IP CONTROL (saline); TOTAL MICE = 8

TABLE 7

EFFECT OF PSP ON TUMOR WEIGHT ON NUDE MICE
IMPLANTED WITH HUMAN RECTAL CARCINOMA

| TUMOR WEIGHT (g) | TUMOR IMPLANTED (on left kidney) | TUMOR METASTASES (outside kidney) |
|---|---|---|
| Saline | 0.015 | 0.097 |
| N = 7 | +0.0040 | +0.0440 |
| PSN | 0.016 | 0.025 |
| N = 9 | +0.0070 | +0.0160 |
| | P > 0.05 | p < 0.001 |

TABLE 8

TREATMENT OF NUDE MICE BEARING
HUMAN LEUKEMIA CELL HL-60 WITH PCV (10 K)

| GROUP (No.) | 2 | 4 | 6 | 8 | 10 | 12* |
|---|---|---|---|---|---|---|
| Treatment: | 3.29 + 0.74 | 3.23 + 0.54 | 2.99 + 0.74 | 3.58 + 0.35 | 3.90 + 0.79 | 4.50 + 1.06 |
| Control: | 3.27 + 0.55 | 3.85 + 0.57 | 4.49 + 0.48 | 6.19 + 1.33 | 10.64 + 2.30 | 17.75 + 3.25 |

8 cases/each group * Treatment days
Tumor Volume: mm$^3$ × 100 = PCV (10 K)

TABLE 9

TREATMENT OF PVC (10 K) TO BALB/C MOUSE BEARING
WITH SP2/O CELL LINE

| GROUP (No.) | 2 | 4 | 6 | 8 | 10 | 12* |
|---|---|---|---|---|---|---|
| Control: | | | | | | |
| Right | 4.74 +0.70 | 5.19 +0.61 | 6.75 +0.91 | 8.87 +0.71 | 15.61 +2.07 | 31.40 +7.19 |
| Left | 3.69 +1.18 | 4.64 +1.40 | 6.28 +1.19 | 9.80 +1.30 | 15.91 +2.52 | 29.78 +6.70 |
| Treatment: | | | | | | |
| Right | 4.37 +0.59 | 4.26 +0.83 | 4.27 +1.47 | 4.29 +1.93 | 6.02 +1.54 | 10.34 +1.78 |
| Left | +4.04 +0.68 | 4.15 +0.81 | 4.02 +1.56 | 3.82 +1.45 | 5.52** +1.09 | 7.78** +1.30 |

Tumor volume: mm 3 × first line: right tumor mass,
Second line: left tumor mass
*Treatment days 5 cases/each group
**Left tumor mass of 2 cases have disappeared.

TABLE 10

TREATMENT OF PCV (10 K) ON $^3$H-TDR Incorporation
IN HL-60 LEUKEMIA CELL AND QZG NORMAL LIVER
CELL FETAL LUNG CELL-HLF

| PSP-D (μg/mL) | Inhibition on cell lines % (X ± SD) | | |
|---|---|---|---|
| | HL-60 | QZG | HLF |
| 12.5 | 40.1 ± 1.90 | 10.7 ± 0.04 | 4.8 ± 0.12 |
| 25 | 66.1 ± 3.27 | 27.2 ± 0.03 | 13.1 ± 0.02 |
| 50 | 81.5 ± 4.79 | 41.9 ± 0.12 | 13.6 ± 0.08 |
| 100 | 91.2 ± 2.26 | 48.4 ± 0.03 | 21.6 ± 0.02 |
| 200 | 96.4 ± 0.58 | 54.3 ± 0.15 | 79.1 ± 0.03 |
| 400 | 99.3 ± 0.10 | 80.7 ± 0.04 | 92.8 ± 0.03 |
| 800 | 99.5 ± 0.10 | 80.8 ± 0.10 | 97.1 ± 0.23 |

*$^3$H-TdR incorporation time: 24 hrs, PSP-D treatment time: 48 hrs.

From the foregoing data, it is apparent that cancer patients treated with purified PCV (10 K or 50 K) from the crude extract of Coriolus versicolor experience relatively low toxic side effects while benefiting therapeutically from the potent anti-tumor affects, which are superior to PSP and PSK. Further, it is apparent that, since the isolated and extracted PCV of the invention have smaller molecular weights (10 K and 50 K) than PSP, they are entirely different from PSP (Mr 100 K) polysaccharide peptide, which has a large molecular weight, and is about from 2 to 10 times larger than the PCVs of the invention.

Moreover, the tumor inhibitory rate of PCV are much higher than those of PSP and PSK, and they inhibited the growth of human leukemia cells, colon cancer cells, hepatoma cells and stomach cancer cells, while exhibiting less cytotoxicity to human normal cells, inclusive of normal liver cells.

It should be noted that, when trifluoroacetic acid (TFA) is used in lieu of $KH_2PO_4$ as the solvent in the HPLC process, the protein content is much higher, and this is borne out by comparing the results in FIGS. 14–17. In the TFA solvent group, the second peak is also in the first peak of the $KH_2PO_4$ solvent group. In other words, the HPLC method of the invention may be accomplished with two different solvents; namely, $KH_2PO_4$ and TFA, and the smaller proteins useful within the context of the invention will be obtained from the first peak of the $KH_2PO_4$ solvent group and the first and second peaks of the TFA solvent group, while the larger proteins will be obtained from the last peaks of the $KH_2PO_4$ and TFA solvent groups.

The PCVs of the invention also possess immunopotentiating affects as they increased white blood cell counts and serum IgG levels. They also increased the organ weight of the liver, spleen and thymus.

Therefore, since the ideal anti-cancer drug is one that directly destroys cancer cells and indirectly stimulates the body's immune system activity while having less toxic side affects on the body, it is apparent that the PCVs of the invention are characterized by all of the desired characteristics for an anti-cancer drug.

Early clinical studies have been performed on 485 cancer patients in Shanghai, China using Pcv. 30 AIDS patients have been treated in Thailand and 10 AIDS patients have been treated in Vancouver, BC using PCV. Early results have been promising.

The foregoing description of the specific embodiments reveal the general nature of the invention so that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation.

All references mentioned in this application are incorporated by reference.

What is claimed is:

1. A method for treating an animal with a tumor comprising administering an effective amount of the pharmaceutical composition comprising a polypeptide isolateable from *Coriolus versicolor*, Cov-1 having a partial amino acid sequence GTAAAKEFERQHM SEQ ID NO:1 and a pharmaceutically acceptable carrier to said animal.

2. A method for treating an animal with a tumor according to claim 1 wherein the tumor metastases are reduced.

3. A method for treating an animal with a tumor according to claim 1 wherein the tumor is a human tumor.

4. A method for treating human cancer patients comprising administering an effective amount of the pharmaceutical composition comprising a polypeptide isolateable from *Coriolus versicolor*, Cov-1 having a partial amino acid sequence GTAAAKEFERQHM SEQ ID NO:1 and a pharmaceutically acceptable carrier thereto.

* * * * *